(12) United States Patent
Warden

(10) Patent No.: US 12,390,395 B1
(45) Date of Patent: Aug. 19, 2025

(54) WEARABLE EYE IRRIGATION SYSTEM

(71) Applicant: Brian Warden, Tifton, GA (US)

(72) Inventor: Brian Warden, Tifton, GA (US)

( * ) Notice: Subject to any disclaimer, the term of this patent is extended or adjusted under 35 U.S.C. 154(b) by 0 days.

(21) Appl. No.: 19/071,139

(22) Filed: Mar. 5, 2025

(51) Int. Cl.
*A61F 9/00* (2006.01)
*A61H 35/02* (2006.01)
*A61M 1/00* (2006.01)

(52) U.S. Cl.
CPC ............... *A61H 35/02* (2013.01); *A61M 1/77* (2021.05); *A61M 2210/0612* (2013.01)

(58) Field of Classification Search
CPC ..... A61H 35/02; A61F 9/0026; A61F 9/0008; A61F 9/04; G02C 11/00; G02C 5/001
See application file for complete search history.

(56) References Cited

U.S. PATENT DOCUMENTS

| | | | | |
|---|---|---|---|---|
| 5,368,582 A | * | 11/1994 | Bertera | G02C 5/001 604/289 |
| 2009/0207373 A1 | * | 8/2009 | Stinson | G02C 11/00 351/158 |
| 2017/0156927 A1 | * | 6/2017 | Richter | A61M 11/005 |

* cited by examiner

*Primary Examiner* — Kai H Weng
(74) *Attorney, Agent, or Firm* — Dale. J. Ream

(57) ABSTRACT

A wearable eye irrigation apparatus resembles a pair of glasses wearable on the nose of the patient and that is in fluid communication with a reservoir of water or saline. A valve mechanism that defines left and right directional outlets is mounted to the frame portion and includes a dial that allows precise control of fluid flow, directing it to one or both eyes singly or simultaneously.

16 Claims, 9 Drawing Sheets

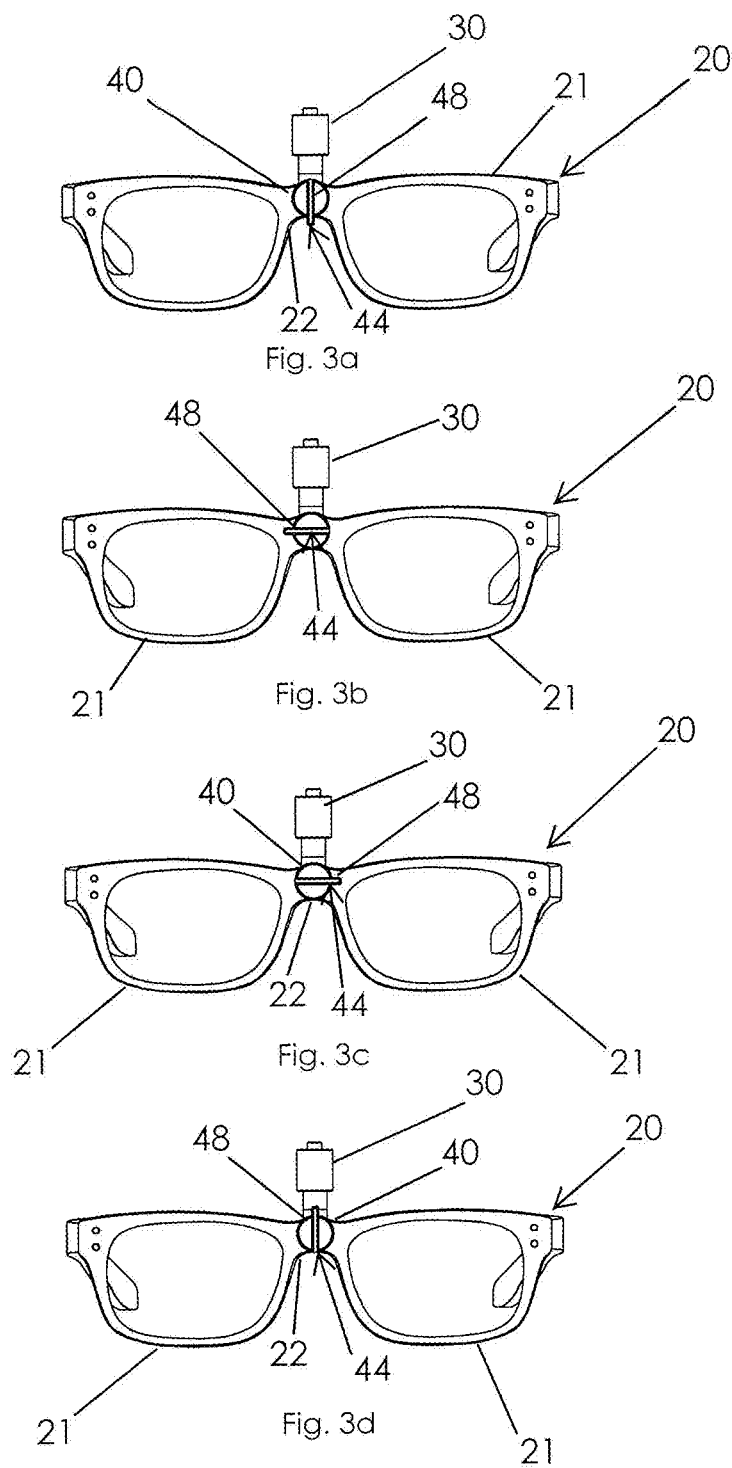

WEARABLE EYE IRRIGATION SYSTEM

BACKGROUND OF THE INVENTION

This invention relates generally to eye irrigation medical devices and, more particularly, to a wearable device that is configured for fluid connection to water or saline and for selective transmission into a patient's left eye, right eye, or both eyes.

Eye irrigation is a critical first-aid and medical procedure used to flush out harmful substances or debris from the eyes. Whether caused by accidents or occupational hazards, foreign substances can pose serious risks to ocular health, making immediate intervention essential. Typical reasons why eye irrigation may be necessary include exposure to cleaning fluids, toxic chemicals used in a manufacturing setting, ocular exposure to sand or other granular materials, or the like.

More particularly, accidental splashing of cleaning agents, such as bleach or ammonia-based solutions, is a common reason why eye irrigation becomes necessary. These substances often contain harsh chemicals that can cause chemical burns, irritation, or even permanent damage to the cornea if not promptly addressed. Flushing the eyes with water or saline helps dilute the chemical concentration, reducing the risk of injury and promoting healing. Further, contact with toxic chemicals in industrial or laboratory environments such as acids, alkalis, or solvents poses a significant threat. These substances can rapidly damage eye tissues, leading to severe pain, swelling, or vision loss. Immediate and thorough irrigation is crucial to neutralize the chemicals and prevent further harm. Still further, granular materials like sand, dust, or metal shavings can become lodged in the eyes, causing discomfort, scratches on the cornea, or infections. Irrigation is essential for washing away these particles to avoid further abrasions and complications.

As a result, many manufacturing facilities are equipped with dedicated eye wash stations to handle emergencies involving chemicals, dust, or debris. These stations typically include eyewash fountains or portable units that provide a steady stream of water or saline for immediate use. Having such stations readily available ensures rapid intervention, reducing the risk of prolonged exposure. For more severe cases, patients may require professional care in an emergency room (ER). Medical personnel use specialized equipment and techniques to thoroughly cleanse the eyes and assess the extent of the injury. While effective, this method can be time-intensive and may require transporting the patient, delaying initial treatment. In less severe cases, individuals may perform eye irrigation themselves or with the help of a bystander. This is often done using household items like a clean cup of water, bottled water, or saline solution. While this method provides immediate relief, it may not be as thorough or effective as professional treatments.

In an ER setting, the standard method for eye irrigation involves the use of a Morgan lens or similar device. The lens is a soft, flexible tube connected to an IV bag of saline or sterile water, which delivers a continuous flow of fluid to the affected eye. The process ensures comprehensive cleansing and helps neutralize or remove irritants.

Although presumably effective for its intended purpose, the traditional ER procedure has notable drawbacks. The insertion of a Morgan lens can be uncomfortable for the patient and requires trained personnel to administer. The process can also be time-consuming, as setting up the equipment and monitoring the irrigation may delay treatment for other injuries. Additionally, this method limits mobility, as the patient must remain in a fixed position during the procedure.

There are additional reasons why traditional eye stations and even traditional emergency room procedures are inadequate. More particularly, regular eye wash stations have major downfalls:

1. they require the patient to be standing or even leaning forward, which in some cases is not possible due to patient condition.
2. Corneal reflexes are strong and when exposed to a high pressure tap water, many patients keep their eyes closed. When patients do open their eyes it's very brief and most of the volume of the water is hitting their face rather than irrigating the eyes.
3. Water often runs into a patient's mouth or nose adding to discomfort and inability to tolerate it.

Therefore, it would be advantageous to have a wearable eye irrigation apparatus that includes a pair of glasses wearable on the face of a patient that is configured for connection to a reservoir of irrigation fluid and to direct that irrigation fluid in the direction of one or both of the patient's eyes. Further, it would be advantageous to have a wearable eye irrigation apparatus that includes a Luer lock for tubular communication to the reservoir of irrigation fluid. In addition, it would be desirable to have a wearable eye irrigation apparatus that includes a directional stopcock or valve that is selectively movable to direct the irrigation fluid toward one or both of a patient's eyes.

SUMMARY OF THE INVENTION

The wearable eye irrigation apparatus resembles a pair of glasses wearable on the nose of the patient and that is in fluid communication with a reservoir of water or saline. A valve mechanism that defines left and right directional outlets is mounted to the frame portion and includes a dial that allows precise control of fluid flow, directing it to one or both eyes simultaneously. This design provides several advantages, including ease of use, namely that the glasses may be quickly donned by the patient and that minimizes the need for specialized training or assistance. Further, the apparatus is less restrictive of patient movement and may reduce the duration of the irrigation procedure. By combining functionality with user-friendly features, this innovative approach has the potential to revolutionize eye irrigation, enhancing both accessibility and effectiveness in emergency and non-emergency scenarios.

Therefore, a general object of this invention is to provide a wearable eye irrigation apparatus having a framework like that of traditional glasses that is configured for fluid communication with a reservoir of irrigation fluid and that includes a valve that is adjustable for directing the irrigation fluid in the direction of the patient's left eye, right eye, or both eyes simultaneously.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 2b is a front view of the eye irrigation apparatus as in FIG. 2a;

FIGS. 3a to 3d are front views of the eye irrigation apparatus as in FIG. 2b, each showing a systematic quarter turn of the adjustment mechanism (e.g., a handle) that results in a dispensing of irrigation fluid through a left directional outlet, a right directional outlet, or both directional outlets of a multi-directional dispenser valve, respectively, according to the present invention;

FIG. 4b is a sectional view taken along line 4b-4b of FIG. 4a;

FIG. 5b is a sectional view taken along line 5b-5b of FIG. 5a;

FIG. 6b is a sectional view taken along line 6b-6b of FIG. 6a;

FIG. 7b is a sectional view taken along line 7b-7b of FIG. 7a;

FIG. 8b is a sectional view taken along line 8b-8b as in FIG. 8a;

DESCRIPTION OF THE PREFERRED EMBODIMENT

Figure 1:
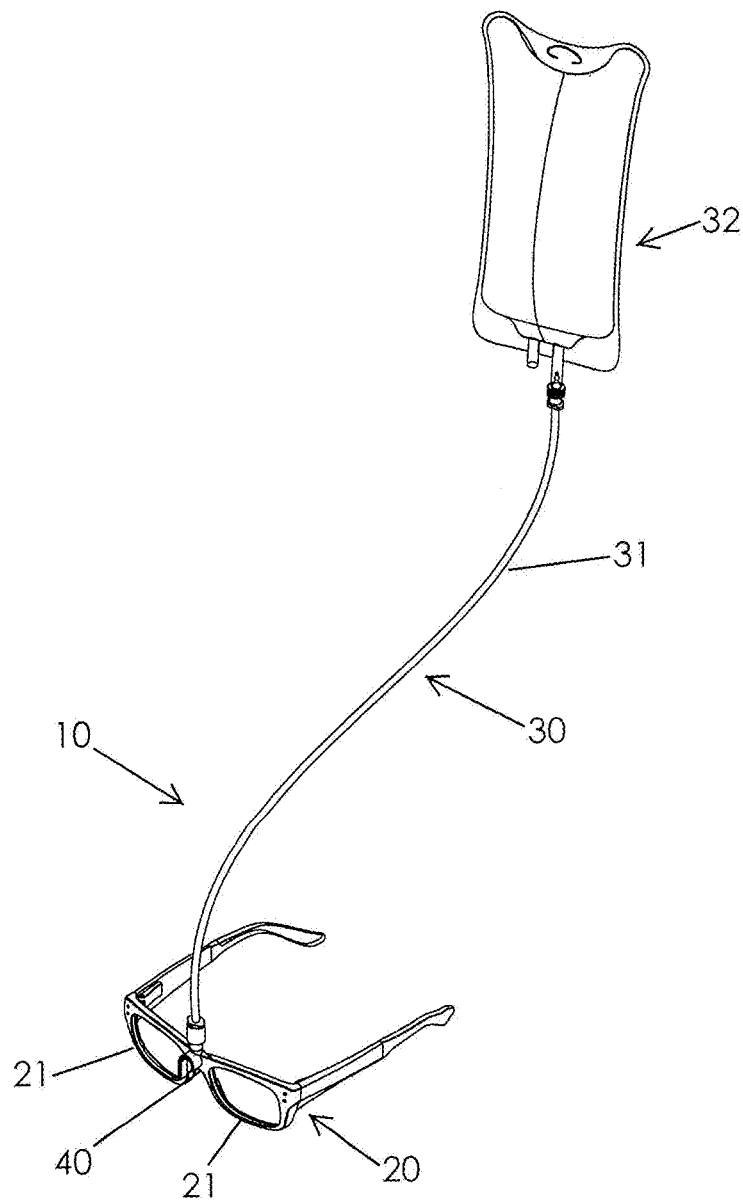
FIG. 1 is a perspective view of a wearable eye irrigation apparatus according to the present invention.
Figure 2A:
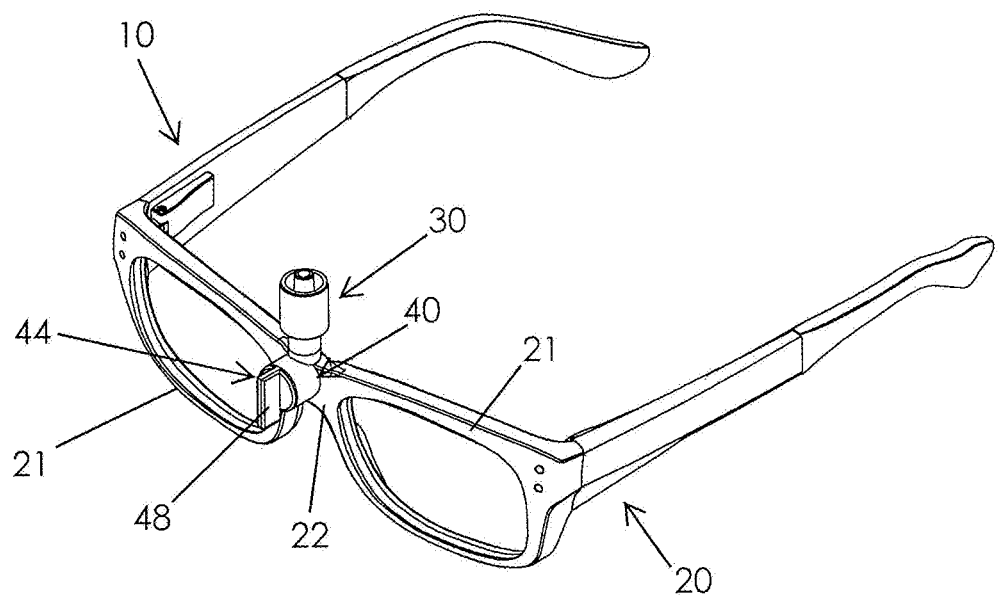
FIG. 2a is another perspective view of the eye irrigation apparatus as in FIG. 1.
Figure 2B:
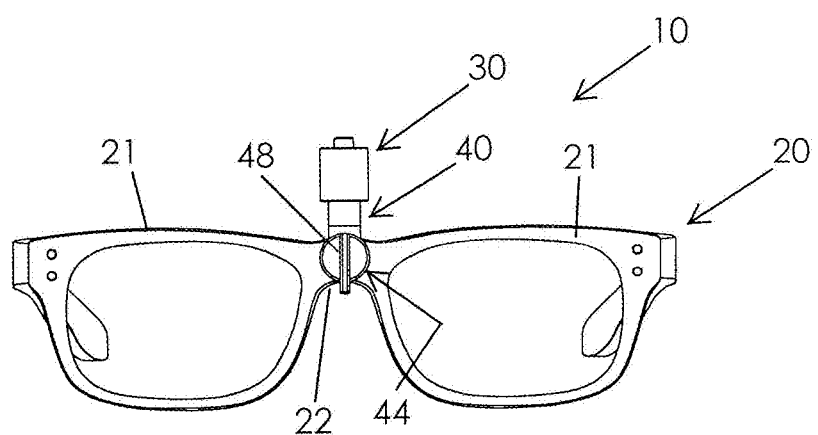

A wearable eye irrigation apparatus according to a preferred embodiment of the present invention will now be described with reference to the accompanying drawings. The wearable eye irrigation apparatus 10 includes a frame portion 20, and access portion 30, and a multi-directional dispensing valve 40.

In a critical aspect, the eye irrigation apparatus 10 of the present invention is wearable on the face of a patient and is configured for targeted irrigation of a single eye or irrigation of both eyes simultaneously. More particularly, the irrigation apparatus 10 includes a frame portion 20 that is indicative of a pair of eyeglasses configured to rest upon the nose of a patient prior to and during operable irrigation of the patient's eyes. For instance, the frame portion 10 may include a plastic or metal framework having a pair of viewing members 21 and having a bridge member 22 that is situated in between the viewing members 21. Stated another way, the viewing members 21 may also be referred to as the rims that hold the glass or plastic lenses that are ground/constructed according to a prescribed parameter that resulted from an optometrist-led examination. Obviously, however, the viewing members 21 do not include functional lenses but, rather, are akin to safety glasses. Further, the frame portion 20 that is indicative of a pair of glasses includes a pair of temples—also referred to as the arms that extend rearwardly from the rims and rest atop a patient's ears. The temples may be pivotally coupled to the rims with hinges and may terminate with temple tips that are bent or angled so as to be captured behind a patient's ears.

In another important aspect, the bridge member 22 may have an arched configuration for resting comfortably atop the nose of a patient although nose pads may be coupled to the rims for a more comfortable fit upon a patient's nose. In an embodiment, the position of the frame portion 20 may involve adjustments to the configuration of the temple arms or nose pads. Importantly, adjustments to the frame portion 20 enable the frame portion 20 to be positioned in a desirable alignment proximate and adjacent to the patient's eyes that are in need of irrigation.

In another aspect of the present invention is a means for accessing irrigation fluid that may then be dispensed to the patient's eyes. The preferred means for accessing irrigation fluid will be referred to herein as the "access portion" 30 of the wearable eye irrigation apparatus 10. More particularly, the access portion 30 may be a tubular structure 31 that may be releasably coupled to a reservoir 32 of irrigation fluid, the irrigation fluid being water or saline or the like. Preferably, the tubular structure 31 may be similar to intravenous tubing and may be referred to by its gauge or radius. It is understood that the tubular structure 31 may be disconnected from the reservoir 32 such that the reservoir 32 may be refilled or completely replaced whether that may become necessary after or even during an irrigation event. In an embodiment, the tubular structure of the access portion 30 is a Luer Lock. A Luer-Lock connector is a type of syringe and needle attachment system used in medical practice to ensure a secure and leak-proof connection between the syringe and needle. The connector may essentially be intravenous tubing having opposed open ends for connecting the reservoir 32 to the multi-directional dispensing valve 40.

In another critical aspect, the wearable eye irrigation apparatus 10 includes a multi-directional dispensing valve 40 coupled to the frame portion 20 and, preferably, to the bridge member 21 because the bridge member 21 is geometrically situated between a patient's eyes when the frame portion 20 is donned on the face of the patient. The dispensing valve 40 may have a generally cylindrical or round configuration having a generally continuous sidewall that defines an interior area, the sidewall also defining a left directional outlet 41, a right directional outlet 42 that is spaced apart and generally opposite the left directional outlet 41. In an embodiment, the directional valve 40 may be described as having "at least one directional outlet" and, preferably, a left directional outlet 41 and a right directional outlet 42. Preferably, each outlet includes a nozzle that is configured to focus or even accelerate irrigation fluid passing therethrough as will be described in greater detail later.

Figure 9:
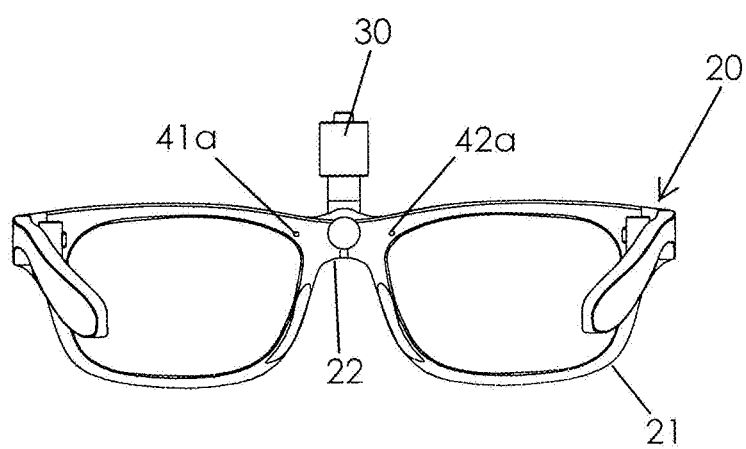
FIG. 9 is a rear perspective view of the irrigation apparatus as in FIG. 2b.

It will be understood that each outlet and associated nozzle is directionally aimed laterally and rearwardly toward a patient's eyes. As will be described later, the multi-directional dispensing may include a selector mechanism 44 that is movable and operable to align the access portion 30 (which is in fluid communication with the irrigation reservoir 32 with respective directional outlets). valve In another aspect, the multi-directional dispensing valve 40 includes an internal connector channel 45 movably mounted in the internal area. Preferably, the internal connector channel 45 has a linear and tubular configuration through which irrigation fluid may flow when the internal connector channel 45 is coupled to a tubular inlet 31a of the access portion 30. Describing the fluid flow of the dispensing valve 40 in even more detail, it will be understood that the structure referred to as the interior connector channel 45 may include a first section and a second section connected to the first section at a 900 angle, i.e., at a T-shaped junction. It will be understood that the T-shaped configuration of the interior connector channel 45 positioned inside the cylindrical valve 40 enables the selective alignment with left and right outlets as the selector mechanism 44 rotates the valve as described above. As shown in FIG. 9, the frame portion 20 defines an auxiliary connector channel 23 extending from the valve outlet 41, 42 to openings 41a, 42a, respectively, the outlets being situated in the rear so as to direct irrigation fluid anatomically toward a patient's eyes.

Figure 4A:
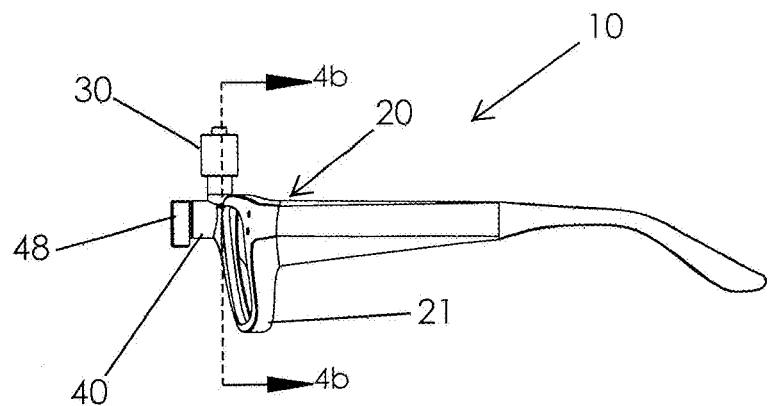
FIG. 4a is a side view of the wearable eye irrigation apparatus as in FIG. 2b.
Figure 4B:
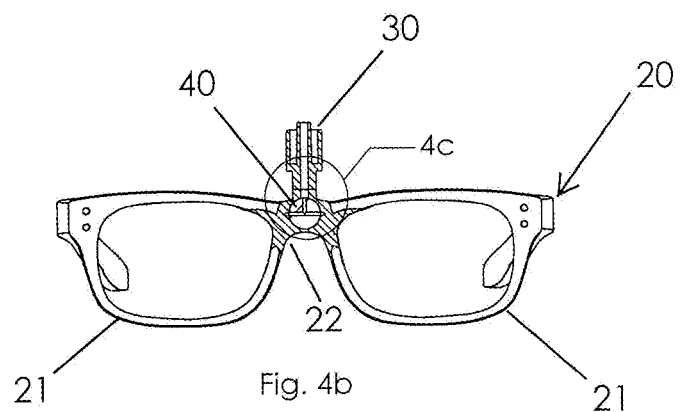
Figure 4C:
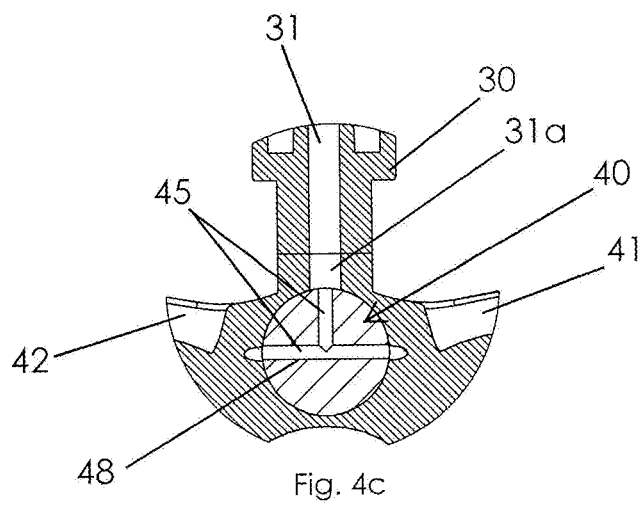
FIG. 4c is an isolated view on an enlarged scale taken from FIG. 4b and illustrates the valve configuration that directs irrigation fluid to both eyes of a patient.
Figure 5A:
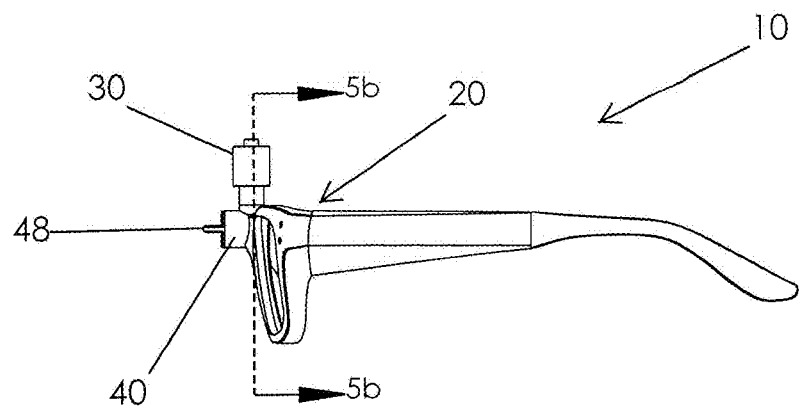
FIG. 5a is a side view of the wearable eye irrigation apparatus as in FIG. 2b.
Figure 5B:
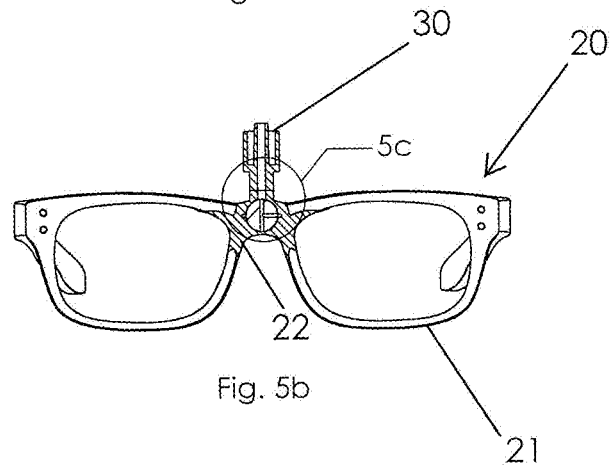
Figure 5C:
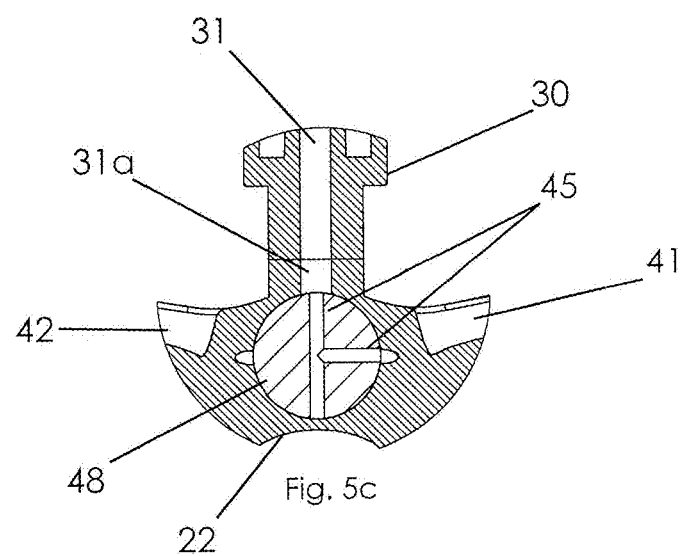
FIG. 5c is an isolated view on an enlarged scale taken from FIG. 5b and illustrates the valve configuration that directs irrigation fluid toward only a left eye of a patient.
Figure 6A:
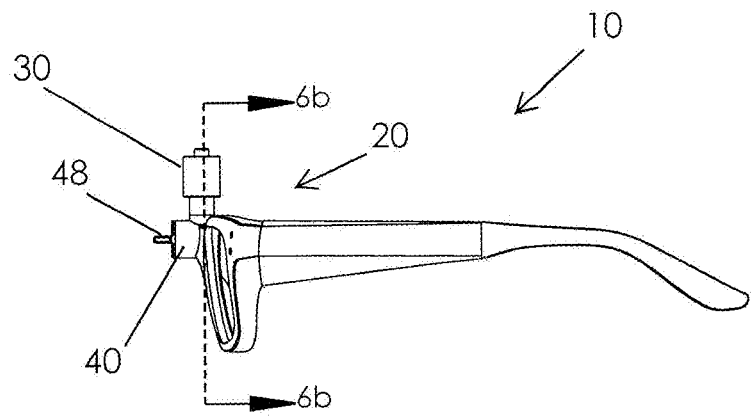
FIG. 6a is a side view of the wearable eye irrigation apparatus as in FIG. 2b.
Figure 6B:
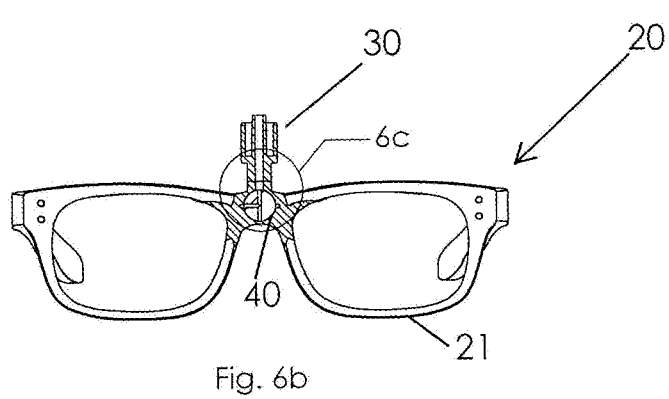
Figure 6C:
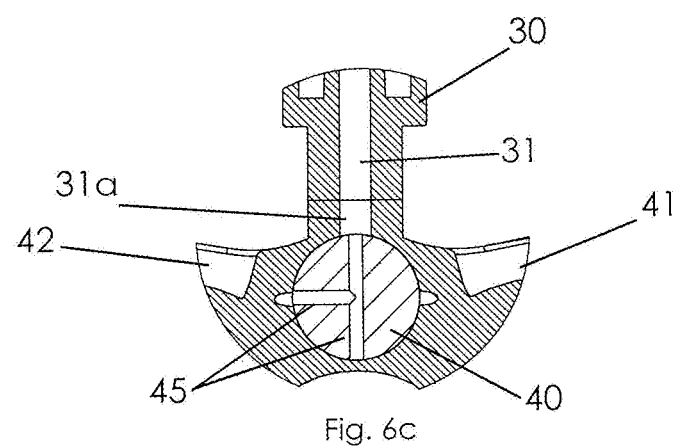
FIG. 6c is an isolated view on an enlarged scale taken from FIG. 6b and illustrates the valve configuration that directs irrigation fluid toward only a right eye of a patient.
Figure 7A:
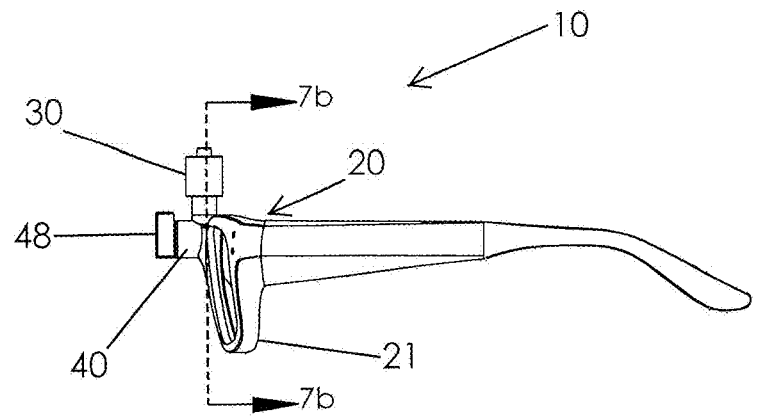
FIG. 7a is a side view of the wearable eye irrigation apparatus as in FIG. 2b.
Figure 7B:
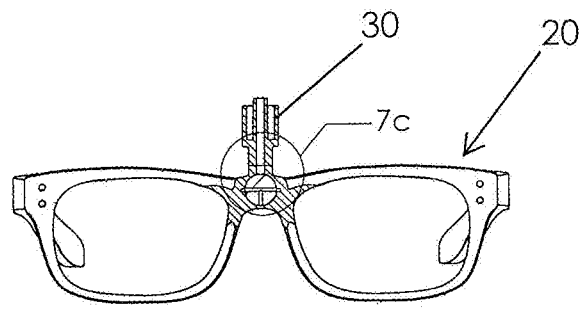
Figure 7C:
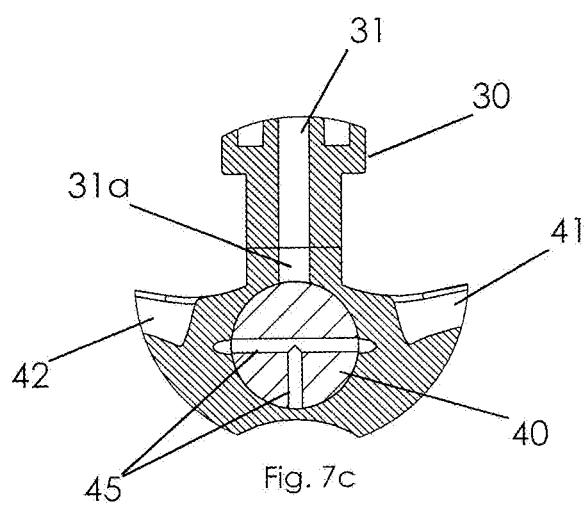
FIG. 7c is an isolated view on an enlarged scale taken from FIG. 7b and illustrates the valve configuration that is shut off.
Figure 8A:
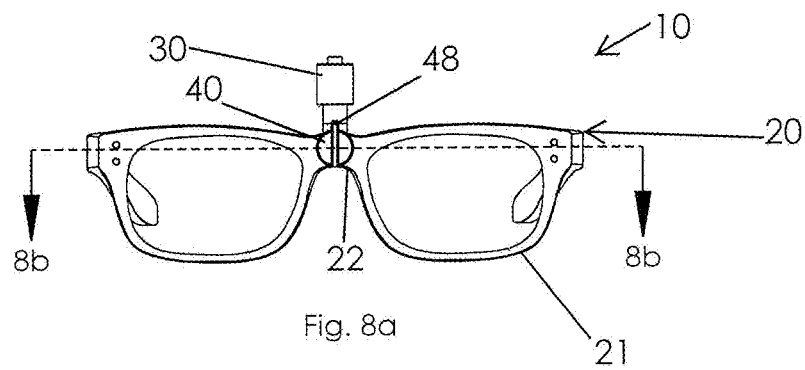
FIG. 8a is a side view of the wearable eye irrigation apparatus as in FIG. 1.
Figure 8B:
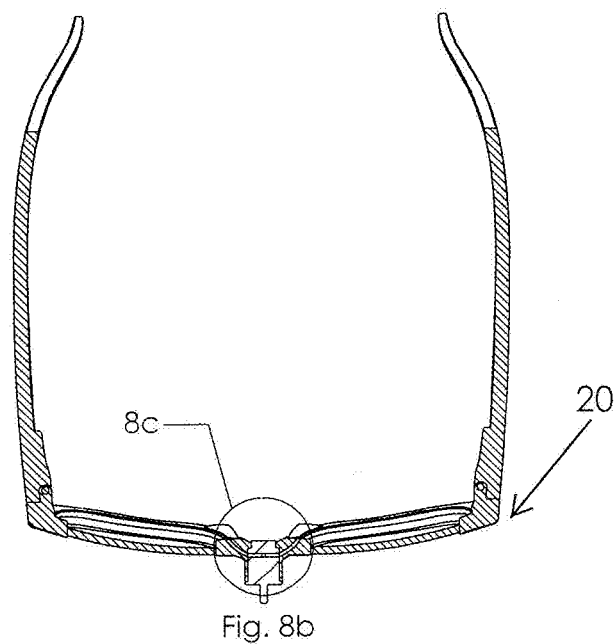
Figure 8C:
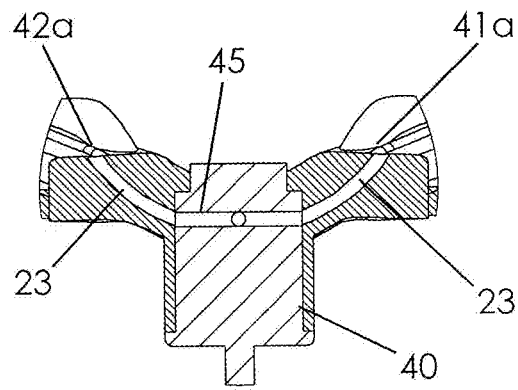
FIG. 8c is an isolated view on an enlarged scale taken from FIG. 8b and from an angle that illustrates a complete fluid channel extending between opposed left and right outlets.

Described in greater detail, the selector mechanism 44 may be a dial that is coupled to the internal connector channel 45 and may be incrementally rotated in a circular motion. Further, the circular and rotational movement of the internal connector channel 45 is operable to align the internal connector channel 45 to direct irrigation fluid from the reservoir 32 to the left directional outlet 41, the right directional outlet 42, or both simultaneously, respectively. The illustrations accompanying this specification show each of these alignments. For instance, FIG. 5c illustrates the internal connector channel 45 directing irrigation fluid to the left directional outlet 41. FIG. 6c illustrates the internal connector channel 45 directing irrigation fluid to the right directional outlet 42. FIG. 4c illustrates the internal connector channel 45 directing irrigation fluid to both outlets simultaneously. And, FIG. 7c shows the internal connector channel 45 rotated to a configuration not in fluid communication with the irrigation fluid (via the access portion 31).

In an embodiment, the dial includes a lever handle 48 extending laterally. Rotation of the lever handle 48 causes corresponding rotation of the dial and alignment of the internal connector channel 45. It is understood that rotation of the handle 48 provides leverage and causes a coordinated rotation of the dial itself. And, as described above, circular motion of the dial results in alignment of the internal connector channel 45 between the access portion 30 and respective outlets for a fluid flow of irrigation fluid therebetween.

While the detailed description above is primarily directed toward the wearable apparatus 10, the present invention may also be described as a method for irrigating a patient's eyes using the wearable apparatus. A method includes positioning the framework portion 20 on the face of a patient, operably connecting the access portion 30 to a reservoir 32 of irrigation fluid, and appropriately manipulating the selector mechanism 44 (a dial) to appropriately aligned the internal connector channel 45 with the outlets as described above.

It is understood that while certain forms of this invention have been illustrated and described, it is not limited thereto except insofar as such limitations are included in the following claims and allowable functional equivalents thereof.

What is claimed is:

1. A wearable eye irrigation apparatus comprising:
   a frame portion constructed in the form of a pair of eyeglasses that includes a pair of viewing members and a bridge member intermediate said viewing members that is configured to rest upon a patient's nose;
   an access portion comprising a tubular structure in fluid communication with an irrigation reservoir containing a quantity of irrigation fluid;
   a multi-directional dispensing valve mounted to said bridge member and in fluid communication with said access portion, the dispensing valve defining at least one directional outlet and a selector mechanism for selectively aligning the access portion with the at least one directional outlet;
   wherein said at least one directional outlet includes a left directional outlet and a right directional outlet spaced apart laterally from said left directional outlet;
   wherein said multi-directional dispensing valve defines an internal area and includes an internal connector channel movably mounted in said internal area, said internal connector channel having a tubular configuration for directing the irrigation fluid when in fluid communication with the access portion.

2. The apparatus as in claim 1, wherein said selector mechanism is a dial coupled to said internal connector channel, wherein said dial is configured for circular motion and is operable to selectively align said internal connector channel with said tubular structure of the access portion and with said left and right directional outlets, respectively.

3. The apparatus as in claim 2, wherein said dial includes a lever handle coupled to said internal connector channel and extending laterally away therefrom such that rotation of said lever handle causes congruent rotation of said dial.

4. The apparatus as in claim 2 wherein said internal connector channel has a T-shaped configuration.

5. The apparatus as in claim 1, wherein said left directional outlet and said right directional outlet include a nozzle, respectively.

6. The apparatus of claim 1, wherein the frame portion is adjustable to fit varying facial dimensions of patients.

7. The apparatus of claim 1, wherein the irrigation reservoir is detachably connected to the tubular structure to facilitate replacement or refilling of irrigation fluid.

8. The apparatus of claim 2, wherein the dial provides incremental flow adjustment for precise control of irrigation fluid delivery to either the left or right directional outlet, or both simultaneously.

9. A method for irrigating a patient's eyes, comprising:
   positioning a wearable eye irrigation apparatus on the patient's face, the apparatus including:
   a frame configured as a pair of eyeglasses, said frame including a pair of viewing members and a bridge member situated between said pair of viewing members such that said frame is configured to rest on the patient's nose;
   an access assembly including a tubular structure in fluid communication with an irrigation reservoir containing irrigation fluid; and
   a multi-directional dispensing valve mounted on the bridge member and in fluid communication with the access assembly, the dispensing valve including at least one directional outlet and a selector mechanism for controlling fluid flow direction;

aligning the tubular structure of the access assembly with the at least one directional outlet using the selector mechanism; and dispensing irrigation fluid through the aligned directional outlet to irrigate the patient's eye;

selectively aligning the access assembly with:

a left directional outlet to irrigate the patient's left eye; or aright directional outlet to irrigate the patient's right eye;

adjusting an internal connector channel situated within the dispensing valve, so that the internal connector channel directs the irrigation fluid to a selected directional outlet.

10. The method as in claim 9, wherein aligning the access assembly further comprises rotating a dial coupled to the internal connector channel to adjust alignment with the left or right directional outlet.

11. The method as in claim 10, further comprising rotating a lever handle connected to the dial, wherein the rotation of the lever handle causes corresponding rotation of the internal connector channel for alignment with the directional outlet.

12. The method as in claim 10, further comprising simultaneously aligning the internal connector channel with both the left and right directional outlets to allow fluid flow through both outlets.

13. The method as in claim 9, further comprising directing the irrigation fluid through a nozzle included in the left directional outlet or the right directional outlet to enhance directional flow during eye irrigation.

14. The method as in claim 9, further comprising adjusting the frame of the wearable system to accommodate the patient's facial dimensions before positioning said frame on the patient's face.

15. The method as in claim 9, further comprising detaching the access assembly from the irrigation reservoir to refill or replace the irrigation fluid.

16. The method as in claim 10, further comprising incrementally adjusting the dial to control the flow of irrigation fluid dispensed through the left directional outlet, the right directional outlet, or both directional outlets simultaneously.

* * * * *